United States Patent [19]

Wunder et al.

[11] 4,224,236
[45] Sep. 23, 1980

[54] PROCESS FOR THE MANUFACTURE OF OXYGEN-CONTAINING CARBON COMPOUNDS FROM SYNTHESIS GAS

[75] Inventors: Friedrich Wunder, Flörsheim am Main; Hans-Jürgen Arpe, Kelkheim; Ernst I. Leupold, Neu-Anspach; Hans-Joachim Schmidt, Königstein, all of Fed. Rep. of Germany

[73] Assignee: Hoechst Aktiengesellschaft, Frankfurt am Main, Fed. Rep. of Germany

[21] Appl. No.: 25,032

[22] Filed: Mar. 29, 1979

[30] Foreign Application Priority Data

Apr. 4, 1978 [DE] Fed. Rep. of Germany ....... 2814427
Jun. 10, 1978 [DE] Fed. Rep. of Germany ....... 2825598
Nov. 18, 1978 [DE] Fed. Rep. of Germany ....... 2850201

[51] Int. Cl.² .............................................. C07C 27/06
[52] U.S. Cl. .......................... 260/449 R; 260/449 M; 260/449.6 R; 260/449.6 M

[58] Field of Search ....... 260/449 R, 449 M, 449.6 R, 260/449.6 M

[56] References Cited

U.S. PATENT DOCUMENTS

| 4,014,913 | 3/1977 | Ellgen et al. | 260/449 R |
| 4,096,164 | 6/1978 | Ellgen et al. | 260/449 R |
| 4,125,553 | 11/1978 | Cropley | 260/449 R |
| 4,136,104 | 1/1979 | Hwang et al. | 260/449 R |

*Primary Examiner*—Howard T. Mars
*Attorney, Agent, or Firm*—Curtis, Morris & Safford

[57] ABSTRACT

Acetic acid, ethanol, acetic aldehyde and possibly the secondary products thereof are prepared by the catalytic reaction of carbon monoxide and hydrogen. The catalyst contains applied onto a carrier, metallic rhodium, halide ions and magnesium salts or complex compounds of magnesium or compounds of magnesium with oxides of elements from groups III to VI of the Periodic Table.

11 Claims, No Drawings

PROCESS FOR THE MANUFACTURE OF OXYGEN-CONTAINING CARBON COMPOUNDS FROM SYNTHESIS GAS

The invention provides a process for the manufacture of oxygen-containing carbon compounds having preferably 2 carbon atoms in the molecule, especially the manufacture of acetic acid, ethanol, acetaldehyde and possibly the secondary products thereof, by reaction of carbon monoxide with hydrogen.

In German Auslegeschriften Nos. 2,503,233 and 2,503,204 it has been disclosed that the reaction in the gaseous phase of synthesis gas, that is, mixture of carbon monoxide and hydrogen, in the presence of rhodium metal-containing catalysts yields substantially mixtures of oxygen-containing products having 2 carbon atoms in the molecule, such as acetic acid, ethanol and/or acetaldehyde. The selectivity with respect to the individual compounds depends on the reaction conditions and can be influenced in favor of ethanol by adding iron salts.

Furthermore, German Offenlegungsschrift No. 2,628,463 proposes to improve the activity of rhodium-containing catalysts by adding manganese (or maintaining their activity while reducing the rhodium amount) without substantially decreasing the selectivity with respect to the oxygen-containing compounds. However, the increased activity of the catalysts results in an increased amount of by-products, which requires additional expenditure for their separation and, possibly, utilization. German Offenlegungsschrift No. 2,628,463 discloses for example in the Table that the most active therein catalysts cited there attain a space/time yield of more than 350 g (up to more than 400 g) of oxygen-containing $C_2$ products per liter of catalyst and hour, but that the total selectivity towards these $C_2$ products does not exceed 60%, relative to reacted carbon monoxide. At least 40% of the reacted carbon monoxide is converted to other products, for example hydrocarbons.

It is the object of this invention to improve the selectivity with respect to oxygen-containing $C_2$ products of rhodium metal-containing catalysts for the reaction of synthesis gas, thereby increasing the profitability of such a process for these technologically important intermediate products.

In accordance with this invention, it has been found that activity and/or selectivity of the rhodium metal catalysts are improved when they contain as co-catalyst magnesium salts or magnesium complex compounds or compounds of magnesium with oxides of elements of the IIIrd to VIth group of the Periodic Table, and halide ions.

The subject of the invention is therefore a process for the manufacture of acetic acid, ethanol, acetaldehyde and the secondary products if any thereof by reaction of carbon monoxide with hydrogen in the presence of rhodium metal-containing carrier catalysts, wherein the catalysts contain in addition halide ions and magnesium salts and/or magnesium complex compounds and/or compounds of magnesium with oxides of elements of the IIIrd to VIth group of the Periodic Table.

Thus, a novel co-catalytically active system is provided which, as compared to the previously known cocatalysts (manganese and iron), displays an improved total selectivity with respect to the cited oxygen-containing compounds (acetic acid, ethanol, acetaldehyde and their secondary products, if any). Surprisingly, and in contrast to manganese and iron which exist in several valence stages and the catalytic properties of which are generally based on the change in valences (redox catalysts), magnesium having only one stable valence (that is, bivalent magnesium) has been found to influence the selectivity. Therefore, it can be assumed that the function of magnesium in combination with the halide ions required in accordance with this invention is fundamentally different from that of manganese or iron in the mechanism of the conversion of synthesis gas to oxygen-containing $C_2$ products. It was furthermore not to be expected that this action increases the efficiency and selectivity of rhodium in such a manner that the profitability of the process is substantially improved.

Oxygen-containing carbon compounds obtained with high selectivity in the process of the invention are acetic acid, ethanol and/or acetaldehyde, and additionally products which may be formed therefrom under the reaction conditions in a subsequent reaction, for example esterification or condensation, such as ethyl acetate and the diethylacetal of acetaldehyde. The amount of other oxygen-containing compounds having 3 or more carbon atoms in the molecule is very low, that is, normally below 10 mol %, relative to reacted carbon monoxide. The total selectivity with respect to oxygen-containing $C_2$ compounds, including products converted to ethyl acetate and acetaldehyde-diethylacetal, is generally above 75%, relative to reacted carbon monoxide. The remaining carbon monoxide is converted to the cited oxygen-containing products having 3 or more carbon atoms in the molecule and substantially to methane and other gaseous hydrocarbons, including, to a smaller extent, carbon dioxide.

Suitable magnesium compounds are the simple inorganic or organic salts of magnesium such as the chloride, bromide, nitrate, formate or acetate, and the oxide, hydroxide or carbonate of magnesium, if they are converted to the above salts by treatment with mineral or carboxylic acids. Alternatively, complex compounds of magnesium with inorganic or organic ligands such as potassium-magnesium trichloride, magnesium-hexamine dichloride, or magnesium-acetylacetonate may be used.

Especially suitable are compounds of magnesium with oxides of elements of the IIIrd to VIth group of the Periodic Table, for example neutral or synthetic aluminates, aluminumsilicates, metasilicates, orthosilicates, titanates, zirconates or chromites of magnesium; these compounds being optionally used simultaneously as carrier substances for the rhodium.

On the other hand, magnesium can be linked by ion exchange to cation exchangers which are stable under the reaction conditions and suitable as carriers for the rhodium, for example the natural or synthetic aluminum silicates known as molecular sieves.

As halides there may be used the chlorides, bromides or iodides of metals of the Ist to VIIIth group of the Periodic Table, because only the anion is relevant. The halides of magnesium or rhodium which may, for example, be formed on the carrier by reaction of oxides, hydroxides or carbonates of these two elements applied onto the carrier with organic compounds splitting off hydrogen halide (such as 1,1-dichloroethane) are especially preferred.

Suitable catalyst carriers are usual carrier materials having different specific surfaces; however, carriers which have a specific surface of from 50 to 1000 m$^2$/g are preferred. Examples are silicic acid, natural or synthetic silicates of elements from groups II to VIII (i.e., for example, the silicates of magnesium, calcium, aluminum, rare earths, titanium, zirconium, manganese), and aluminum oxide, zirconium oxide, thorium oxide, vanadium pentoxide, zeolites or spinels.

For preparing the catalysts, the carriers are soaked in solutions of the active components or impregnated with them either simultaneously or in subsequent steps, after which the catalyst is reduced. When using oxides of elements of groups III to VI as carriers, a preferred catalyst preparation method is the following: the magnesium compound and the halide (which may be identical) are applied onto the carrier, and the impregnated carrier is converted completely or partially to a mixed oxide of magnesium and the element of the IIIrd to VIth group of the Periodic Table, for example magnesium silicate, by sintering at elevated temperature and subsequently impregnating it with the rhodium compound.

Reduction of the rhodium compound to metallic rhodium is carried out by treatment with reducing agents such as hydrogen or carbon monoxide, or mixtures thereof or, for example, methanol at temperatures above 300° C., preferably from 350° to 550° C. Generally, it is advantageous not to use the reducing agent in a concentrated state but with an additional amount of inert gas such as nitrogen, carbon dioxide or noble gases.

The concentration of rhodium, magnesium and halides in the catalysts may vary within wide limits; generally the values are from 0.1 to 20 weight % for rhodium, from 0.1 to 25 weight % for magnesium and from 0.01 to 20 weight % for the halide ions. Preferred are catalysts containing from 1.0 to 10 weight % of rhodium, from 0.1 to 20 weight % of magnesium and 0.05 to 15 weight % of halides.

For carrying out the process of the invention, gas mixtures consisting either completely or substantially of carbon monoxide and hydrogen, optionally containing other components in addition, such as nitrogen, argon, carbon dioxide or methane, are passed over the catalyst. The molar ratio of carbon monoxide and hydrogen may vary within wide limits. Preferred are molar ratios of from 5:1 to 1:5 and especially from 3:1 to 1:3.

The reaction temperatures are generally from 175° to 375° C., preferably from 200° to 350° C., and the reaction pressure is generally from 1 to 300 bars, preferably from 20 to 200 bars.

It is advantageous to adjust temperature and pressure in such a manner that a high selectivity with respect to the oxygen-containing compounds is insured and that the exothermic formation of methane promoted by elevated temperatures is maintained at a low level. High pressure and low temperatures are therefore preferred. The conversion rate of carbon monoxide should be generally below 50%, because a higher rate may cause increased formation of by-products which, in addition to methane, carbon dioxide and gaseous hydrocarbons, may comprise high molecular weight liquid hydrocarbons and oxygen-containing substances.

The process is preferably carried out in the gaseous phase, for which the usual solid bed reactors may be used, the catalyst layer of which should be advantageously thin in order to insure a good heat dissipation. Reactors provided with moving catalyst bed or fluidized beds reactors are likewise suitable.

Alternatively, the synthesis gas may be reacted in the presence of the solid and finely distributed catalyst suspended in inert solvents and/or reaction products.

According to an especially preferred embodiment of the invention, the reaction is carried out in the gaseous phase in a circulating gas apparatus, where the unreacted gas mixture is recycled to the reactor after separation of the condensible reaction products. This operation mode is particularly economic and, because of the fresh gas being diluted by the recycled gas containing less hydrogen, it allows for the application of elevated temperatures and to obtain high space/time yields at unchanged selectivity. Suitable circulating gas apparatus are those provided with interior or exterior gas circulation.

When carrying out the process of the invention it has been observed that, although the catalysts display a high initial activity and an excellent selectivity of the carbon monoxide reaction towards the oxygen-containing $C_2$ compounds, this activity and selectivity may gradually decrease after prolonged use of the catalysts, at operation times of more than about 500 hours. Life of these catalysts could therefore be limited.

It has now been found that this life is considerably extended when during the reaction of the synthesis gas, magnesium salts or magnesium compounds which are volatile under the reaction conditions are fed either continuously or discontinuously to the reaction zone together with the gaseous reactants.

The advantage of this preferred embodiment of the invention resides in the fact that the activity and selectivity of the catalysts containing rhodium, magnesium and halides used for the reaction remain unchanged even after more than 1000 hours.

Magnesium salts or magnesium compounds which are volatile under the reaction conditions and therefore capable of being fed in gaseous form to the reaction zone together with one or more of the reactants, are for example, magnesium chloride, bromide, iodide, acetylacetonate, ethylate, isopropylate, magnesium-aluminumethylate and -isopropylate or magnesium salts of aliphatic monocarboxylic acids having from 1 to 4 carbon atoms in the molecule. Preferably, magnesium chloride or magnesium acetate is used, but alternatively those magnesium salts or magnesium compounds which can be converted to the halide by reaction with hydrogen halide, or to the corresponding carboxylates by reaction with aliphatic monocarboxylic acids, such as the oxide, hydroxide or the carbonates of magnesium are suitable.

The volatile magnesium salts or magnesium compounds are fed together with the gaseous reactants to the reaction zone which operation can be carried out according to various methods. Thus, the magnesium compounds in dissolved form, for example as solution in water, ethanol or acetic acid, can be injected into the hot gas current before the catalyst layer. Alternatively, prior to their entry into the reaction zone, all or part of the reaction gases can be contacted at elevated temperature with a solution or melt of the magnesium compound, or these gases may be passed over such a solution or melt. According to an especially preferred operation mode, all or part of the reactants are passed at elevated temperature over the volatile magnesium compound being present in solid form, which is thus vaporized without the use of an additional solvent. In this case, the volatile magnesium compounds may be applied onto an inert carrier material such as silicic acid, aluminum oxide or charcoal. The magnesium compound to be vaporized may be present either inside or outside of the reactor and preferably, it is arranged in such a manner that the heated reactants first pass through a zone containing the magnesium compound, and then through that reactor zone which contains the catalyst. In principle, these zones may be merged into each other or optionally mixed.

The volatile magnesium compounds can be introduced either continuously or discontinuously into the reaction zone. In the case of the preferred continuous addition, the amount of magnesium compound is from 0.01 to 200 ppm, preferably 0.1 to 50 ppm, relative to the weight of the gas current passed over the catalyst. In the case of discontinuous addition, even larger amounts may be fed to the gas mixture, depending on the addition time. By means of the temperature and the volume of the gas passed over the magnesium compound the dosage of the latter can be controlled.

Subsequently, the gas current containing magnesium compound, carbon monoxide and hydrogen is reacted on contact with the catalyst containing rhodium, magnesium and halide.

When operating in a circulating gas apparatus according to the especially preferred embodiment of the invention, where after separation of the condensible reaction products the unreacted gas mixture is recycled to the reactor with addition of fresh synthesis gas, the magnesium compound can be added either to the circulating gas, the fresh synthesis gas or to the mixture of both gases.

Life of the catalysts can be prolonged alternatively by another method than that of adding magnesium compounds, that is, during the reaction of the synthesis gas hydrogen halide or volatile organic halogen compounds not containing any sulfur or nitrogen in the molecule and splitting off hydrogen halide under the reaction conditions are fed continuously or discontinuously to the reaction zone together with the gaseous reactants.

This preferred operation mode of the process of the invention brings about the same advantage as that of adding magnesium compounds, that is, the activity and selectivity of the catalysts containing rhodium, magnesium and halides are nearly unchanged even after more than 1000 hours.

Hydrogen halides, hydrogen chloride, bromide or iodide or mixtures thereof may be used or produced in the reaction zone by reaction of halogen with hydrogen or synthesis gas. Hydrogen chloride is the preferred hydrogen halide.

Volatile organic halogen compounds not containing any sulfur or nitrogen in the molecule and splitting off hydrogen halide under the reaction conditions are alkyl, aryl and aralkyl halides having one or more halogen atoms in the molecule, such as dichloromethane, carbon tetrachloride, ethyl iodide, 1,1-dichloroethane, allyl chloride, tert.-butyl chloride or benzyl chloride, furthermore saturated or unsaturated halocarboxylic acids, haloaldehydes, haloalcohols, haloketones or haloethers of the aliphatic, cycloaliphatic or aromatic series, for example mono-, di- or trichloroacetic acid, iodoacetic acid, bromoacetone, alpha, beta-dichloro-diethyl ether, 3-chloro-crotonic acid (cis or trans), or p-chlorobenzoic acid. Suitable are furthermore carboxylic acid halides such as acetyl chloride, bromide or iodide or mono-, di- or trichloroacetyl chloride, which under the influence of the water formed in the synthesis gas reaction very easily split off hydrogen halide. The preferred halogen compound is acetyl chloride.

It is not required that the volatile organic halogen compound be split off hydrogen halide quantitatively; small amounts of hydrogen halide split off are sufficient to substantially extend the life of the catalysts.

The hydrogen halides or the organic compounds splitting off hydrogen halide are fed to the reaction zone together with the gaseous reactants according to various methods. Thus, the hydrogen halides or organic halogen compounds may be introduced into the hot gas current in dissolved form, for example as a solution in water, ethanol or acetic acid. Alternatively, the total reaction gas—or in a side current part of this gas stream—may be passed over the solid or liquid organic halogen compound before its entry into the reaction zone. By correspondingly adjusting the gas amount, the pressure and the temperature, the intended amount of halogen compound can be added in accordance with its partial pressure. Furthermore, the organic halogen compounds may be likewise applied in impregnated form onto an inert carrier such as silicic acid, aluminum oxide or charcoal, over which the reactants, that is, CO and $H_2$, are then passed.

The hydrogen halides or the volatile organic halogen compounds can be introduced either continuously or discontinuously into the reaction zone. In the case of the preferred continuous addition, their concentration is from 0.01 to 500 ppm, preferably 0.1 to 100 ppm, relative to the weight of the gas current passed over the catalyst. In the case of discontinuous addition, even larger amounts may be fed to the gas mixture, depending on the addition time. The amounts added are in this case inversely proportional to the time of addition.

Subsequently, the gas current containing the hydrogen halide or the volatile organic halogen compound, carbon monoxide and hydrogen is reacted on contact with the catalyst containing rhodium, magnesium and halide.

When operating in a circulating gas apparatus according to the especially preferred embodiment of the invention, where after separation of the condensible reaction products the unreacted gas mixture is recycled to the reaction with addition of fresh synthesis gas, the hydrogen halide or the organic halogen compound can be added either to the circulating gas, the fresh synthesis gas, or to the mixture of both gases.

The two methods described for extending the life of the catalysts, i.e., the addition of magnesium compounds or the addition hydrogen halide or organic halogen compound can be performed simultaneously.

The following examples illustrate the invention without limiting its scope. The conversion rates and selectivity are expressed in mol %. The other parts and percentages are by weight unless otherwise stated.

EXAMPLES 1 TO 7 AND COMPARATIVE EXAMPLES 1 AND 2

(A) General test description

The apparatus consists of a heatable reactor tube of corrosion-proof steel having a length of 1 m and an inner diameter of 16 mm, provided with a coaxially arranged thermometer casing having an exterior diameter of 6 mm, a subsequent condenser, a receiver for the condensate, and a compressor for recycling part of the uncondensed gases to the reactor (circulating gas). 100 ml each of the catalysts indicated below are charged. After flushing of the apparatus with nitrogen, first a pressure of 80 bars is adjusted by means of synthesis gas having the following composition: 49% by vol. of CO, 49% by vol. of $H_2$, 1% by vol. of $CO_2$, 1% by vol. of $N_2$ (and small amounts of other components), and the reactor is heated to 300° C. During the heating and in the course of the test, 500 Nl/h of synthesis gas having the above composition are fed to the circulating gas via the suction face of the compressor, and passed over the catalyst together with the circulating gas. The gas mixture leaving the reactor is cooled (by brine cooling) in the condenser to about 5° C., and the condensed portions are collected in the receiver. The uncondensed residual gas is recycled to the reactor via the compressor after having been mixed with fresh synthesis gas. In order to maintain the pressure and to discharge by-products, part of the residual gas is let off as waste gas via a pressure regulating valve.

According to this operational method the catalysts as described below are tested. In the Table, there are listed the duration of the tests, the space/time yields of oxygen-containing $C_2$ products per liter of catalyst and hour at the start and the end of the tests, the percentage distribution of acetic acid, acetaldehyde and ethanol, relative to the $C_2$ portion of the condensate, and the selectivity with respect to these compounds (in mol % of CO, relative to reacted CO). Small amounts of ethyl acetate or acetaldehyde-diethylacetal obtained are calculated as acetic acid, ethanol or acetaldehyde.

(B) Preparation of catalysts

EXAMPLE 1

40 g of a silicic acid having a BET surface of 270 $m^2/g$, a pore volume of 1.22 ml/g, a bulk density of 0.4 kg/l, a pH of 7.4 (measured on granules having a diameter of 2 to 3 mm) and containing 99.35% of $SiO_2$ and 0.2% of Na are impregnated with a solution of 10.4 g of magnesium chloride (56% strength) in 45 ml of water, dried for 2 hours at 70° C. and 2 hours at 150° C. Subsequently the catalyst is sintered for 30 minutes at 900° C. After cooling, it is impregnated with a solution of 5.3 g of $RhCl_3.x\ H_2O$ (37.8% of Rh) in 45 ml of water, and dried in the same manner as described above. In a flow tube made of glass, the catalyst is reduced by passing over it 30 Nl/h of hydrogen for 3 hours at 450° to 500° C. under normal pressure. After the reduction, it contains 4.2% of Rh, 3.1% of Mg and 1.1% of Cl. At the start of the test, the space/time yield is 415 g of oxygen-containing $C_2$ compounds per liter of catalyst and hour, which compounds are distributed as follows: 52.3% of acetic acid, 4.36% of acetaldehyde and 4.1% of ethanol.

COMPARATIVE EXAMPLE 1

(using a magnesium-free and halogen-free catalyst)

5.6 g of $Rh(NO_3)_3.2\ H_2O$ (31.3% of Rh) are dissolved in 45 ml of water and applied onto 40 g of the silicic acid carrier as described in Example 1. After a 2 hours' standing, the catalyst is dried at 80° C. and 260 mbars by passing 1 Nl/h of nitrogen over it. The catalyst is reduced as described in Example 1 and contains 4.2% of Rh.

COMPARATIVE EXAMPLE 2

(using a halogen-free catalyst)

A solution of 14.5 g of $Mg(NO_3)_2.6\ H_2O$ in 43 ml of water is applied onto 40 g of the silicic acid carrier as described in Example 1. The impregnated carrier is dried at 120° C. and subsequently sintered for 30 minutes at 800° C. After cooling, it is impregnated with a solution of 5.9 g of $Rh(NO_3)_3.2\ H_2O$ (31.3% of RH) in 45 ml of water, dried at 80° C. under a reduced pressure of 260 mbars and 1 Nl/h of nitrogen, and reduced as described in Example 1. After the reduction, the catalyst contains 4.2% of Rh and 3.1% of Mg.

EXAMPLE 2

(reduction in the reactor)

As carrier there is used a natural commercial magnesium silicate which, after washing and drying, has the following composition: 65.5% of $SiO_2$, 3.6% of $Al_2O_3$, 0.5% of $Fe_2O_3$ and 14.0% of MgO. The bulk density is 537 g/l and the pore volume 0.99 ml/g.

54 g of this carrier (100 ml) are impregnated with a solution og 6.3 g of $RhCl_3.x\ H_2O$ (37.8% of Rh) in 49 ml of water, and dried at 150° C. The catalyst is introduced into the reactor without reduction, heated without pressure to 425° C. under a nitrogen current of 30 Nl/h, and reduced at this temperature by passing over it 60 Nl/h of a mixture of carbon monoxide and hydrogen in a volume ratio of 1:1. Different from the general test description, the catalyst is now cooled to 225° C., a pressure of 80 bars is established by means of synthesis gas, and the catalyst is heated to the reaction temperature of 300° C. After the reduction, the catalyst contains 4.2% of Rh, 7.8% of Mg and 0.95% of Cl.

EXAMPLE 3

Separately prepared solutions of 21 g of $MgBr_2.6\ H_2O$ in 20 ml of water and 8.6 g of $RhBr_3.2\ H_2O$ (27.2% of Rh) in 14 ml of water are united and immediately applied onto 40 g of the silicic acid carrier described in Example 1. Subsequently, the catalyst is dried at 80° C. and 260 mbars, and reduced as indicated in Example 1.

EXAMPLE 4

There are dissolved separately from each other 13.4 g of $MgI_2$ in 20 ml of water and 8.9 g of $RhBr_3.2\ H_2O$ (27.2% of Rh) in 23 ml of water. These two solutions are cooled to 10° C., united at this temperature and immediately applied onto 40 g of the silicic acid carrier described in Example 1. Subsequently, the catalyst is dried at 90° C., under a reduced pressure of 260 mbars and under nitrogen, and reduced as indicated in Example 1.

EXAMPLE 5

40 g of a silicic acid carrier composed as described in Example 1 are impregnated with a solution of 13.3 g of $KMgCl_3.6\ H_2O$ and 5.6 g of $RhCl_3.x\ H_2O$ (37.8% of Rh) in 38 ml of water, dried under normal pressure at 120° C. and reduced as indicated in Example 1.

EXAMPLE 6

Pyrogenic titanium dioxide (prepared from $TiCl_4$ by flame hydrolysis) is mixed with 2% of kaolin, pasted with water, dried and crushed to a grain size of from 0.1 to 1 mm. Subsequently, tablets having a diameter of 3 mm are molded and sintered at 600° C.

80 g (corresponding to 100 ml) of these tablets are impregnated with a solution of 20 g $MgCl_2.H_2O$ (56% strength) and 7.5 g of $RhCl_3.x\ H_2O$ (37.8% of Rh) in 45 ml of water, dried at 150° C. and reduced according to the method described in Example 1. The catalyst contains 3% of Rh, 3% of Mg and 1.03% of Cl.

EXAMPLE 7

Most finely distributed zirconium dioxide is given a tablet form as described in Example 6. 85 g (corresponding to 100 ml) of these tablets are impregnated with a solution of 22 g of $MgCl_2 \cdot x\ H_2O$ (56% of $MgCl_2$) and 16.5 g of $RhCl_3 \cdot x\ H_2O$ (37.8% of Rh) in 48 ml of water. The catalyst is dried at 90° C. and reduced as indicated in Example 1.

(C) Test results

The results are listed in the following Table.

TABLE

Reaction conditions: 80 bars, 300° C.,
starting gas 500 Nl/h $CO:H_2$ = 1:1, catalyst volume 0.1 l
AcOH = acetic acid, AcH = acetaldehyde, EtOH = ethanol

| | Catalyst composition | | | Test duration hours | Space/time yield oxygen-containing $C_2$-compd. in g/l.h | | Composition of $C_2$-compound in wt.-% | | | Selectivity mol % CO converted to | |
|---|---|---|---|---|---|---|---|---|---|---|---|
| Example | Rh [wt.-%] | Mg [wt.-%] | carrier | | start of test | end of test | AcOH | AcH | EtOH | $C_2$-compd. | $CH_4$ |
| 1 | 4.2 | 3.1 | $SiO_2$ | 412 | 415 | 398 | 52.3 | 43.6 | 4.1 | 82.2 | 8.5 |
| Comp. Ex. 1 | 4.2 | — | $SiO_2$ | 194 | 61 | 42 | 45.5 | 18.7 | 35.8 | 51.1 | 35.6 |
| Comp. Ex. 2 | 4.2 | 3.1 | $SiO_2$ | 194 | 256 | 238 | 58.6 | 28.8 | 12.6 | 66.7 | 18.9 |
| 2 | 4.2 | 8.4 | $MgSiO_3$ | 322 | 402 | 377 | 32.3 | 7.2 | 60.5 | 78.0 | 14.2 |
| 3 | 4.2 | 3.1 | $SiO_2$ | 186 | 395 | 362 | 54.7 | 36.0 | 9.3 | 75.2 | 19.4 |
| 4 | 4.6 | 2.2 | $SiO_2$ | 186 | 390 | 358 | 48.8 | 33.5 | 17.7 | 74.6 | 18.5 |
| 5 | 4.2 | 2.3 | $SiO_2$ | 212 | 398 | 370 | 38.2 | 19.5 | 42.3 | 80.5 | 11.2 |
| 6 | 3.0 | 3.0 | $TiO_2$ | 186 | 368 | 346 | 41.5 | 17.9 | 40.6 | 78.6 | 12.5 |
| 7 | 6.0 | 3.0 | $ZrO_2$ | 162 | 412 | 388 | 35.5 | 24.3 | 40.2 | 75.4 | 16.7 |

EXAMPLE 8

As carrier there is used natural, commercial magnesium silicate which after washing and drying has the following composition: 65.5% of $SiO_2$, 3.6% of $Al_2O_3$, 0.5% of $Fe_2O_3$ and 14.0% of MgO. The bulk density is 537 g/l and the pore volume 0.99 ml/g.

108 g (200 ml) of this carrier are impregnated with a solution of 12.6 g of $RhCl_3 \cdot x\ H_2O$ (37.8% of Rh) in 98 ml of water, and dried at 150° C. In a flow tube of glass, the catalyst is reduced by passing over it 75 Nl/h of hydrogen at 375°-425° C. for 3 hours under normal pressure. After the reduction, it contains 4.2% of Rh, 7.8% of Mg and 1.05% of Cl. 100 ml of the reduced catalyst are introduced into a vertically positioned flow tube reactor made of corrosion-proof steel, having an inner diameter of 16 mm and a length of 1 m, and provided with exterior salt melt heating, thermometer, preheater, subsequent condenser, receiver for the condensate, pressure regulating valve and a compressor for circulating part of the residual gas mixture. The preheater is charged with 100 ml of a silicic acid carrier which was impregnated with a solution of 15 g of magnesium acetate in 40 g of water and subsequently dried.

After flushing with nitrogen, first a pressure of 120 bars is established by means of a synthesis gas (49% by vol. of CO, 49% by vol. of $H_2$, 1% by vol. of $CO_2$, traces of $N_2$), and the catalyst is heated to 280°. During the heating and in the further course of the test, 300 Nl/h of the synthesis gas are added to the circulating gas via the suction face of the compressor and passed together with the circulating gas first through the preheater heated to 280° C. and subsequently through the reactor. The gas mixture leaving the reactor is cooled to about 5° C. in a condenser cooled by brine, and the condensed portions are collected in the receiver. The uncondensed residual gas is recycled via the compressor to the preheater and the reactor after having been mixed with the fresh gas. In order to maintain a constant pressure and to discharge by-products, part of the residual gas is let off as waste gas via a pressure regulating valve.

41 g of oxygen-containing $C_2$ compounds (22 g of ethanol, 12 g of acetic acid, 7 g of acetaldehyde) are obtained per hour in the form of an aqueous solution, which corresponds to a space/time yield of 410 g per liter of catalyst and hour. The CO conversion rate is on the average 31% of starting substance, and the selectivity with respect to the oxygen-containing $C_2$ products is 82.3%, relative to converted carbon monoxide. Space/time yield, CO conversion rate and selectivity are unchanged even after more than 1500 hours.

Small amounts (about 2% relative to the cited $C_2$ products) of ethyl acetate or acetaldehyde diethylacetal were calculated as acetic acid, ethanol or acetaldehyde and are contained in the indicated data. This is likewise valid for the following Examples.

COMPARATIVE EXAMPLE 3

Operations are as in Example 8; however, the preheater is charged with pure unimpregnated silicic acid. Under test conditions being for the rest as in Example 8 and with the use of 100 ml of catalyst having the composition as indicated there, the space/time yield of the first 500 hours is 400 g of oxygen-containing $C_2$ products per liter of catalyst and hour, after a total of 740 hours it is 365 g/lh, after 1000 hours 348 g/lh, and after 1680 hours 312 g/lh only; the percental composition of the product mixture being the same as in Example 8. The conversion rate of CO decreases within the same period of time from 31 to 29.9%, and the selectivity with respect to the oxygen-containing products from more than 80% to 72.5%, relative to converted carbon monoxide.

EXAMPLE 9

100 g of a silicic acid as indicated in Example 1, the pore volume being however 1.27 ml/g, are impregnated with a solution of 18.75 g of magnesium chloride (56% strength) in 112 ml of water, and dried for 2 hours at 70° C. and 2 hours at 150° C. Subsequently, the catalyst is sintered for 30 minutes at 900° C. After cooling, the silic acid is impregnated with a solution of 14.25 g of RhCl$_3$.x H$_2$O 37.8% of Rh) in 112 ml of water, and dried in the same manner as indicated above. In a flow tube of glass the catalyst is reduced by passing over it 75 Nl/h of hydrogen for 3 hours at 400°–450° C. under normal pressure. After the reduction, it contains 4.6% of Rh, 2.3% of Mg and 0.7% of Cl.

100 ml of the catalyst are introduced into a reactor as described in Example 8 which, different from Example 8, is not provided with a compressor. After flushing with nitrogen, 235 Nl/h of a gas mixture containing 49% by vol. of carbon monoxide, 49 vol. % of hydrogen, 1 vol. % of carbon dioxide and small amounts of nitrogen are passed over the catalyst at 120 bars and 280° C., that is, in one single passage, not according to the circulating gas operation mode. In the preheater heated to 280° C., too, 100 ml/h of an aqueous 0.07% magnesium acetate solution are injected into the hot gas mixture.

After having left the reactor, the reaction gases are cooled to 5° C. and the uncondensed portions are depressurized. 28 g of acetic acid, 8.5 g of acetaldehyde and 3.5 g of ethanol are obtained per hour as condensate. The CO conversion rate is 35.1%, the selectivity with respect to oxygen-containing C$_2$ products is 81.0%, relative to converted carbon monoxide. Space/time yield, CO conversion rate and selectivity are unchanged even after more than 1000 hours.

COMPARATIVE EXAMPLE 4

Operations are as in Example 9; however, instead of the aqueous magnesium acetate solution 10 ml/h of distilled water are introduced into the preheater. The space/time yield after 200 hours is 395 g of oxygen-containing C$_2$ products, after 600 hours it is 360 g and after 1000 hours 290 g, each per liter of catalyst and hour. The percental composition of the C$_2$ products is the same as that indicated in Example 9. The CO conversion rate decreases within this period of time from 35% to 32.5%, and the selectivity towards the oxygen-containing C$_2$ products from 80.7% to 63.5%.

EXAMPLE 10

100 g of a silicic acid as described in Example 9 are impregnated with a solution of 14.7 g of magnesium chloride (56% strength) in 112 ml of water and dried for 2 hours at 70° C. and 2 hours at 150° C. Subsequently, it is sintered for 30 minutes at 800° C. After cooling, the silicic acid is impregnated with a solution of 14.0 g of RhCl$_3$.x H$_2$O (38.0% of Rh) in 112 ml of water, and dried in the same manner as indicated above. The catalyst is reduced in a flow tube of glass by passing over it for 3 hours 75 Nl/h of hydrogen at 400°–450° C. and under normal pressure. After the reduction, it contains 4.5% of Rh; 1.8% of Mg and 0.6% of Cl.

100 ml of the reduced catalyst are introduced into a reactor according to Example 9. After flushing with nitrogen, 250 Nl/h of a gas mixture containing 49 vol. % of carbon monoxide, 49 vol. % of hydrogen, 1 vol. % of carbon dioxide and small amounts of nitrogen are passed over the catalyst at 100 bars and 290° C. In the preheated heated to 290° C., too, 10 ml/h of an aqueous 0.1% hydrochloric acid are injected into the hot gas current.

After leaving the reactor, the reaction gases are cooled to 5° C., and the uncondensed portions are depressurized. 27 g of acetic acid, 6.5 g of acetaldehyde and 2.5 g of ethanol are obtained per hour as condensate, which corresponds to a space/time yield of 360 g/l h. The CO conversion rate is 28.9%, the selectivity towards the oxygen-containing C$_2$ products is 82.5%, relative to converted carbon monoxide. The space/time yield, the CO conversion rate and the selectivity are unchanged even after 1000 hours.

Small amounts (about 3% relative to the cited C$_2$ products) of ethyl acetate or acetaldehyde-diethylacetal are calculated as acetic acid, ethanol or acetaldehyde and are contained in the above data. This is likewise valid for the following Examples.

COMPARATIVE EXAMPLE 5

Operations are as in Example 10; however, instead of the dilute hydrochloric acid, 10 ml of distilled water per hour are introduced into the preheater. After 240 hours the space/time yield is 345 g of oxygen-containing C$_2$ products, after 600 hours it is 315 g and after 1200 hours it is 240 g, each per liter of catalyst and hour. The percental composition of the C$_2$ products is the same as in Example 10. The CO conversion rate decreases within this period of time from 28.2% to 24.8% and the selectivity towards the oxygen-containing C$_2$ products drops from 81.0% to 64.0%.

EXAMPLE 11

(a) As carrier, a magnesium silicate as described in Example 8 is used. 108 g (200 ml) of this carrier are impregnated, dried and reduced as indicated also in Example 8, and after the reduction, the catalyst contains 4.1% of Rh, 7.5% of Mg and 1.12% of Cl.

100 ml of the catalyst are introduced into a reactor according to Example 10 which, however, different from this Example 10, is provided with a compressor in addition for the circulation of part of the residual gas mixture.

After flushing with nitrogen, first a pressure of 100 bars is adjusted by means of a synthesis gas (49 vol % of CO, 49 vol. % of H$_2$, 1 vol. % of CO$_2$, traces of N$_2$), and the catalyst is heated to 290° C. During the heating and in the further course of the test, 300 Nl/h of the synthesis gas are added to the circulating gas via the suction face of the compressor, and passed together with the circulating gas first through the preheater heated to 290° C. and subsequently through the reactor. 10 ml/h of a 0.1% solution of 1,1-dichloroethane in methanol is dosed into the preheater. The gas mixture leaving the reactor is cooled to about 5° C. in a brine-cooled condenser, and the further operations are as in Example 8.

38 g of oxygen-containing C$_2$ compounds (21 g of ethanol, 10 g of acetic acid and 7 g of acetaldehyde) are obtained per hour in the form of an aqueous solution, which corresponds to a space/time yield of 380 g per liter of catalyst and hour. The CO conversion rate is on the average 28.6% of starting substance, and the selectivity with respect to the oxygen-containing C$_2$ products is 83.3%, relative to converted carbon monoxide. Space/time yield, CO conversion rate and selectivity are still unchanged even after more than 1800 hours.

In three further tests, there was used instead of the 0.1% solution of 1,1-dichloroethane in methanol a solution having the same concentration of (b) monochloroacetic acid in methanol,
(c) benzyl chloride in methanol, and
(d) acetyl chloride in diethyl ether.

Otherwise, the tests were identical to (a). The results were identical as well.

COMPARATIVE EXAMPLE 6

Operations are as in Example 11; however, 10 ml of pure methanol are introduced per hour into the preheater. With the use of 100 ml of catalyst having the composition as indicated in Example 11 and under the same test conditions as described there, the space/time yield of the first 600 hours is 360 g of oxygen-containing $C_2$ products per liter of catalyst and hour, after 1000 hours it is 315 g/l.h and after 1500 hours only 280 g/l.h; the percental composition of the product mixture being identical to that of Example 11. Within the same period of time, the CO conversion rate decreases from 27.9 to 24.1% and the selectivity towards the oxygen-containing $C_2$ products drops from 81.2 to 72.6%, relative to converted carbon moxide.

What is claimed is:

1. A process for the manufacture of acetic acid, ethanol, acetaldehyde and any secondary products thereof which comprises catalytically reacting carbon monoxide and hydrogen using a catalyst, applied onto a carrier, containing metallic rhodium and halide ions in admixture with a co-catalyst of magnesium salts and/or magnesium complex compounds and/or compounds of magnesium with oxides of elements selected from groups III to VI of the Periodic Table and reducing the catalyst at a temperature in the range of 350° to 550° C.

2. The process according to claim 1 wherein the catalyst contains 0.1 to 20 weight percent rhodium, 0.1 to 25 weight percent magnesium and 0.01 to 20 weight percent halide ions.

3. The process according to claim 1 wherein the carrier is selected from the group consisting of silicic acid and magnesium silicate.

4. The process according to claim 1 or 3 further comprising the continuous or discontinuous addition of volatile magnesium salts or magnesium compounds together with the carbon monoxide and hydrogen as gaseous starting materials to the reaction zone during the reaction.

5. The process according to claim 1 or 3 wherein the halide ions are chlorides.

6. The process according to claim 5 wherein the carrier is selected from the group consisting of silicic acid and magnesium silicate.

7. The process according to claim 4 wherein the magnesium salt or magnesium compound used is either magnesium acetate or magnesium chloride.

8. The process according to claims 1, 2 or 3 further comprising the continuous or discontinuous addition of a hydrogen halide or a volatile organic halogen compound not containing any sulfur or nitrogen in the molecule to the reaction zone during the reaction of the gaseous starting components and splitting off hydrogen halide under reaction conditions.

9. The process according to claim 4 further comprising the continuous or discontinuous addition of a hydrogen halide or a volatile organic halogen compound not containing any sulfur or nitrogen in the molecule to the reaction zone during the reaction of the gaseous starting components and splitting off hydrogen halide under reaction conditions.

10. The process according to claim 8 wherein the hydrogen halide is hydrogen chloride.

11. The process according to claim 8 wherein the volatile organic halogen compound is acetyl chloride.

* * * * *